United States Patent [19]

Schmolka

[11] Patent Number: 4,585,647

[45] Date of Patent: * Apr. 29, 1986

[54] METHODS AND COMPOSITIONS FOR INTRAVAGINAL CONTRACEPTION

[75] Inventor: Irving R. Schmolka, Grosse Ile, Mich.

[73] Assignee: BASF Corporation, Wyandotte, Mich.

[ * ] Notice: The portion of the term of this patent subsequent to Jan. 22, 2002 has been disclaimed.

[21] Appl. No.: 672,619

[22] Filed: Nov. 19, 1984

[51] Int. Cl.$^4$ .............................................. A61K 31/74
[52] U.S. Cl. ........................................ 424/45; 424/78; 514/843
[58] Field of Search ..................... 424/45, 78; 514/843

[56] References Cited

U.S. PATENT DOCUMENTS 3,740,421 6/1973 Schmolka .............................. 424/65
4,368,186 1/1983 Vickery et al. ........................ 424/78

FOREIGN PATENT DOCUMENTS 1444334 7/1976 United Kingdom .

OTHER PUBLICATIONS

Chemical Abstracts 82:45617n, 1975, (Veltman).

Primary Examiner—Leonard Schenkman
Attorney, Agent, or Firm—Bernhard R. Swick

[57] ABSTRACT

A pressurized contraception composition in an aerosol container and adapted to form a spray upon release of pressure therefrom which composition is a liquid inside the container and forms a gel on contact with living tissue and process employing same, whereby the composition comprises water, propellant, a polyoxyethylene-polyoxypropylene copolymer, and preferably a sperm function inhibitor.

16 Claims, No Drawings

METHODS AND COMPOSITIONS FOR INTRAVAGINAL CONTRACEPTION

BACKGROUND OF THE INVENTION

After two decades of effort to devise satisfactory contraceptive methods which depend on metabolic control mechanisms (oral contraceptives and progestational inserts) or on intra-uterine mechanical disruption, i.e. intrauterine devices (IUD's); alternative methods which depend on barriers (diaphragms, condoms) and on topical application of spermicides or other contraceptives (intravaginal foams or suppositories) have not become obsolete, and are still in wide use. These methods attract considerable interest due to their safety, freedom from undesirable side effects, and relative accessibility, without the need for a physician's intervention. The present invention relates to compositions for, and methods of, contraception based on topical intravaginal application of spermicides or other antifertility agents which inhibit sperm function.

Present formulations for intravaginal application of sperm function inhibitors are designed to insure coverage of the entire vaginal vault with the active ingredient (usually a surfactant, and typically nonoxynol-9, a nonionic surfactant).

One method for intravaginal application comprises supplying the contraceptive composition in the form of a gel.

The preparation of aqueous gels employing as gelling agents polyoxyethylene-polyoxypropylene block copolymers is well known to those skilled in the art and is taught in several patents including U.S. Pat. Nos. 3,740,421, 3,748,276, and 3,749,465.

U.S. Pat. No. 4,368,186 discloses that compositions designed for intravaginal application containing polyoxyethylene-polyoxypropylene block copolymers in substantial amount, have unexpected inherent spermicidal properties.

While the form of application of the spermicide may be varied, such as, gel, foam, cream, or a suppository designed to disintegrate and spread by means of, for example, an effervescent dissolution process, all of these application methods are basically similar to barrier methods in that they depend in the final analysis, on the spermicide encountering and destroying all sperm which enter the vagina.

For this reason, the present formulations and method of application cannot be considered totally satisfactory solutions to the problem. If they succeed in coverage of the entire vaginal surface, they are inherently messy and unaesthetic. If they fail to do so, they are relatively ineffective; a particular problem with those formulations designed in the form of dissolving suppositories.

It is known in the prior art to apply gels from aerosol containers as can be seen by the following:

U.S. Pat. No. 3,751,562, issued Aug. 7, 1973, to Nichols, discloses an aerosol gel formulation employing an oxyethylated fatty alcohol, mineral oil, iodine and water.

U.S. Pat. No. 4,293,542, issued Oct. 6, 1981, to Lang et al, discloses aerosol formulations which can be an aqueous gel containing oxyethylated fatty alcohols and a gel-forming agent and, as an essential component, a pyridine derivative. Another aerosol gel composition is disclosed in U.S. Pat. No. 4,001,391.

While it is known in the art to apply gel compositions by the use of aerosol-type containers, filling an aerosol container with a gel presents problems.

British No. 1,444,334 discloses an aerosol gel composition which may be employed as a shaving cream and which contains as a gelling agent a polyoxyethylene-polyoxypropylene block copolymer. An essential component of the composition is a water-soluble soap. This patent is concerned with the problem of expelling a gel from an aerosol container and particularly avoiding cavitation around the dip tube. Accordingly, the compressed gas or liquified gaseous propellant is required to be substantially insoluble in the gel so that it can act in the manner of a piston to force the gel from the container without cavitation. Aerosol gel compositions are also described in U.S. patent application Ser. Nos. 513,439; 524,985; 525,147 and 525,148.

SUMMARY OF THE INVENTION

The instant invention relates to a greatly improved method of intravaginal application of a spermicide characterized by greatly improved coverage over prior art methods and a composition employed in such method, whereby the composition is in the form of a gel applied from an aerosol container. As pointed out above and particularly evident from British Pat. No. 1,444,334, there are filling and cavitation problems inherent in the use of gels in aerosol containers. These problems are overcome in accordance with the instant invention by the use of a pressurized composition which may be sprayed from an aerosol container and which is liquid inside the container and forms a gel on contact with living tissue. This is accomplished preferably by the combination of water, propellant, volatile solvent and certain polyoxyethylene-polyoxypropylene block copolymers. As employed throughout the instant specification and claims, the term "solvent" means a solvent for the gel composition of this invention. While the composition itself acts as a sperm function inhibitor, the composition preferably contains a conventional sperm function inhibitor. It may also contain at least one non toxic adjuvant such as other pharmaceuticals, emollients, etc. which are pharmaceutically acceptable and which do not irritate the mucous membrane.

The polyoxyethylene-polyoxypropylene block copolymer has a polyoxypropylene hydrophobe molecular weight of about 3000 to 4500 and the oxyethylene groups constitute 50 to 90 percent preferably 60 to 80 percent of the total weight of the copolymer.

DESCRIPTION OF THE PREFERRED EMBODIMENTS

The aerosol composition of the instant invention should be liquid at ambient temperature, i.e. from about 20° to about 30° C., but upon warming, to about 35° C. or higher should become a viscous gel or a foamy paste-like solid. This may be accomplished by varying the ratio of surfactant and water as well as the amount and type of propellant used. This may also be accomplished by the use of a volatile solvent in the composition, particularly where the propellant is not soluble in the composition or vice versa.

The aerosol composition of the instant invention comprises by weight about 20 to 60 percent water, about 20 to 80 percent propellant, about 7.5 to 30 percent of the polyoxyethylene-polyoxypropylene block copolymer, 0 to about 1.5 percent, preferably about 0.02 to 1.0 percent, of a sperm function inhibitor, about 5 to about 40 percent, preferably about 10 to 25 percent, of a non-propellant volatile solvent, and 0 to about 30 percent, preferably about 5 to 10 percent adjuvants. By the use of a propellant which is also a solvent, the need for a non-propellant solvent is eliminated and thus the amount can be 0. Also the need for any solvent may be eliminated by proper selection of the copolymer and its concentration.

The polyoxypropylene-polyoxyethylene block copolymer of use in the invention is a cogeneric mixture of conjugated polyoxypropylene polyoxyethylene compounds having as a hydrophobe, a polyoxypropylene polymer having a molecular weight of about 3000 to 4500. The polyoxypropylene compounds are prepared by first condensing propylene oxide with an organic compound containing a plurality of reactive hydrogen atoms to prepare a polyoxypropylene polymer having a molecular weight of about 3000 to 4500 and subsequently condensing ethylene oxide therewith. The compounds used in this invention conform to the following general formula:

$$Y[(C_3H_6O)_n-E-H]_x \quad (A)$$

wherein Y is the residue of a water soluble organic compound containing therein x active hydrogen atoms; n is an integer; x is an integer greater than 1; the values of n and x are such that the molecular weight of the compound, exclusive of E, is about 3000 to 4500 as determined by hydroxyl number; E is a polyoxyalkylene chain wherein the oxygen/carbon atom ratio is at least 0.5, and E constitutes 50 to 90 percent of the total weight of the compound.

The polyoxypropylene polymer, which is an intermediate in the preparation of the compounds of use in this invention, has the following structure:

$$Y[(C_3H_6O)_nH]_x \quad (B)$$

wherein Y, n and x are defined as in Formula A above.

The preferred compounds of use in this invention are prepared by condensing ethylene oxide in an amount between 50 and 90 percent of the total weight of the resultant compound, with the polyoxypropylene polymer. These compounds have the following formula:

$$Y[(C_3H_6O)_n(C_2H_4O)_mH]_x \quad (C)$$

wherein Y, n and x are defined as in Formula A and m has a value such that the oxyethylene groups constitute about 50 to 90 percent of the total weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon atom ratio is at least 0.5.

Examples of a water-soluble organic compound containing therein x active hydrogen atoms, the residue of which is Y, are the initiators which may include water, diols such as propane diol, butanediol, triols such as glycerol and trimethylol propane, tetrols such as pentaerythritol as well as initiators containing more than four hydroxyl groups such as hexitol or sucrose. Also, amines and other low molecular weight water-soluble compounds having two or more active hydrogen atoms, such as ethylene diamine or diethylene triamine, may be used as the initiator. Preferably used is propylene glycol. More preferably used is 1,2-propylene glycol.

The propylene oxide used in making the hydrophobic polyoxypropylene polymer, which is an intermediate in the preparation of the compounds used in this invention, may be replaced with up to 30 percent by weight of butylene oxide or ethylene oxide when added as a mixture with the propylene oxide. Also, up to 30 percent by weight of propylene oxide or butylene oxide may be used to replace ethylene oxide, when added as a mixture with ethylene oxide, in preparing the surfactants used in this invention.

When ethylene oxide is condensed with a polyoxypropylene glycol of about 3000 to 4500 molecular weight and derived from a propanediol initiator, the resulting compounds have the following structure:

$$HO(C_2H_4O)_m(C_3H_6O)_n(C_2H_4O)_mH \quad (D)$$

wherein n is defined as set forth with respect to formula A and m has a value such that the oxyethylene groups constitute about 50 to 90 percent of the total weight of the compound.

Surfactants of the invention, conforming to structures C and D above, are those surfactants which have a hydrophobe molecular weight of between about 3000 and 4500 and ethylene oxide groups in amount of from about 50 to 90 percent of the total weight of the surfactant.

A composition which is a liquid inside the container and forms a gel on contact with living tissue which does not include a volatile solvent in the composition may be obtained by the use of a combination of water, non solvent propellant and polyoxyethylene-polyoxypropylene block copolymer. More specifically, by the proper selection of the water/copolymer ratio the composition would be a liquid at ambient temperature (20° C. to 25° C.) and would form a gel on being exposed to body heat at atmospheric pressure. Such composition would have a maximum water-to-copolymer ratio of 5.7:1.

Where the water to copolymer ratio is less than 5.7:1 a volatile solvent is incorporated in the composition which evaporates upon contact with body heat whereby the liquid becomes a gel. The use of the solvent extends the water:copolymer ratio whereby it can be less than 5.7:1. Suitable solvents include alcohols such as methyl, ethyl and propyl, ketones such as dimethyl and ethyl methyl, ethers such as methyl, ethyl, methyl-ethyl, and similar ethers, and chlorinated alkanes such as dichloromethane. A non-volatile solvent such as liquid polyethylene glycols, propylene glycol, glycerol, dipropylene glycol, etc., can be used together with a volatile solvent, provided the mixture is homogeneous.

The propellants can be any one or a blend of the following as examples: propane, isobutane and other petroleum distillates, nitrogen, carbon dioxide, dimethylether, ethylmethylether, methylene chloride, vinyl chloride and fluorochlorohydrocarbons. The latter include Freon 115, pentafluorochloroethane and Freon C-318, octafluorocyclobutane. Where the composition is soluble in the propellant, or where the propellant is soluble in the composition, a non-propellant volatile solvent may not be needed. Such volatile solvent propellants include dimethylether, methylethylether and methylene chloride.

The product may form a foamy gel after expelling from the aerosol container which is firm or rigid and which will form upon body contact. For this purpose, small amounts of conventional foaming agents well known to those skilled in the art such as nonionic, amphoteric, and anionic surfactants may be employed. Such foaming agents include high-foaming ethylene oxide adducts such as fatty alcohol ethoxylates and potassium lauryl sulfates and lauryl ether sulfates. Other examples of such agents are triethanolamine lauryl sulfate, sodium dodecylbenzene sulfonate, water-soluble polyoxyethylene ethers of alkyl-substituted phenols, amine oxides and phosphate ester based surfactants.

In the context of the present invention, "sperm function inhibitor" refers to compounds which render sperm incapable of fertilizing the female subject, whether by immobilizing, altering, or killing the sperm. These agents are in the general contraceptive class, but are distinguished by directing their effects to the capacity of the sperm to fertilize, rather than altering the metabolism of the female, as is the case with, for example, progestational contraceptives. Examples of such sperm function inhibitors include surfactants such as the widely used nonoxynol-9 or 10, or octoxynol-9 or 10, which appear to be spermicidal; certain mercuric salts, which also kill sperm, certain 1-substituted imidazoles which are both spermicidal and spermatostatic—i.e., immobilizing; and peptide or other synthetic inhibitors of the sperm proteases which mediate the fertilization of the ovum. Other sperm function inhibitors include benzalkonium blends and 1-substituted imidazole sulfates. Nonoxynol-9 is a well known spermicide having the chemical name p-nonylphenoxypolyethoxyethanol. Combinations of two or more of the above may also be included.

The spermicidal properties of the water polyoxyalkylene polyol gel alone are clearly advantageous in enhancing the effect of any additional sperm function inhibitor used as an active ingredient. Said gels have been shown to immobilize sperm in vitro and to reduce fertilization in vivo.

The ability of the composition to deliver the active ingredient represents a more sophisticated approach to the problem of intravaginal contraception than has previously been disclosed. Clearly it is necessary, to achieve the goal of contraception, to affect only those sperm which actually enter the uterus. Therefore, if the sperm function inhibitor can be concentrated in the area of the cervix, the pathway through which the sperm must enter and if large amounts of agent are soluble therein, the purpose of the method can be achieved, without an excess of material being required.

By the use of an aerosol container containing the composition of this invention which is a liquid inside the container and forms a gel on contact with living tissue, it is easier to achieve proper placement of the gel near the cervix. This is particularly true if the aerosol container outlet is provided with a small tube several inches in length, making it possible to apply the gel directly to the area of the cervix where the gel is needed. Such tubes are common in the aerosol art particularly exemplified by aerosol containers employed for applying carburetor cleaners to the inside of an automotive carburetor.

Many and various adjuvants are generally also included. The amount of such adjuvants would range from 0 to about 30 percent and where employed the amount would be at least about 1 percent. The preferred amount is about 5 to 10 percent by weight. By way of example, additional pharmaceutical excipients are desirable in the composition. A suitable lower alkylene glycol, such as, for example, glycerin, may be a desirable component. This glycol or glycerol should be present in about 2 percent to 30 percent by weight.

It may also be desirable to buffer the present composition so as to enhance its inherent spermicidal activity. Any suitable compatible buffer solution may be used, that is, weak acids and weak bases and their corresponding salts, to adjust to the desired pH. A useful buffer system for the present invention is the citric acid/citrate system which can be adjusted to an acidic pH to enhance a spermicidal effect. The total percentage of buffering components, should be in the range of 0.5 percent to 2 percent of the total composition. Suitable pH ranges are approximately 3 to 6, preferably 4.5 to 5.

Small amounts of antimicrobial preservatives such as parabens, benzyl alcohol and others, and antioxidants such as BHA, BHT and others may also be included to preserve integrity of the preparation during storage. The percentage of these preservatives should be in the range of 0.01 to 2 percent, preferably 0.5 to 1 percent. Other adjuvants could include proteins, amino acids, electrolytes and other ingredients normally found in body fluids. Humectants, such as propylene glycol may also be included. Further adjuvants could include silicone oils. Also, other adjuvants which impart further desired qualities to the skin may be incorporated in the compositions of the invention, e.g., lanolin or its derivatives, lecithin, higher alcohols, dipelargonate ethers or esters, coconut oil and other fatty esters, and mixtures thereof may generally be used in minor proportions. Furthermore, coloring materials such as dyes and perfumes may be used, if desired.

The method of the invention as practiced, of course, depends on the particular circumstances of the subject, and upon the nature of the active ingredient chosen as the sperm function inhibitor. Generally, the administration of the composition containing the active ingredient should take place between about eight hours to about two minutes prior to sexual intercourse. There appears to be no preferable range within this time frame, and therefore, the convenience of the subject is the paramount consideration. The amount of composition to be applied also varies with the concentration of the active ingredient and the design of the applicator. An effective amount is between 0.5 to 6 ml of the gel for human subjects, with correspondingly larger or smaller amounts for other mammals. Preferably, it is desirable, from an aesthetic standpoint, for human subjects to use a minimum amount of composition, preferably 0.5 to 2 ml total volume, which is facilitated by the accuracy of positioning of the application.

By the use of the aerosol applicator and composition of the invention, the composition can be deposited approximately at the location of the cervix, which is of course the critical surface, whereby a minimal amount of material can be employed.

The following examples are included to further illustrate the present invention. Unless otherwise stated, throughout the application all parts and percentages are by weight and all temperatures are in degrees centigrade.

EXAMPLE 1

A concentrate is prepared from 15 parts of a polyoxyethylene-polyoxypropylene block copolymer of the type shown in formula (D) above, designated herein as copolymer #1, having a polyoxypropylene hydrophobe molecular weight of 4500 and containing oxyethylene groups in the amount of 70 percent of the total copolymer weight, 3 parts glycerine and 82 parts water. Fifty-nine parts of this gel concentrate and 6 parts of isopropanol are placed in an aerosol container. Thirty-five parts by weight of dimethylether propellant are then added through the valve. The contents are shaken, and 1 ml sprayed onto a cervix.

A thin film forms initially after which the dimethylether and isopropanol evaporate forming a coating completely covering the cervix. This becomes a foamy gel as the solvent and propellant evaporate. The composition effectively immobilizes spermatazoa.

EXAMPLE 2

A liquid composition is prepared comprising 25 parts of a polyoxyethylene-polyoxypropylene copolymer, 3 parts of methylethylether, 0.1 part of nonoxynol-9, and 71.9 parts of water.

One hundred parts of the above liquid are placed in an aerosol container, the container is pressurized and sealed with a valve and 50 parts of a propellant, namely dimethylether, are added through the valve. The contents are shaken and 1 ml sprayed onto the cervix. A thin film forms initially completely coating a cervix after which the dimethylether and ethylmethylether evaporate whereby a foamy gel forms on the surface. The composition effectively immobilizes spermatazoa.

The polyoxyethylene-polyoxypropylene copolymer employed, designated herein as copolymer #2, is a polyoxyethylene adduct of a polyoxypropylene hydrophobic base having a molecular weight of said base of about 3200 and wherein the oxyethylene content is about 80 percent of the total weight of the molecule. The polyoxypropylene hydrophobic base is prepared by reacting propylene oxide with a propanediol initiator.

EXAMPLE 3

Example 2 is repeated using 100 parts of a liquid composition comprising 25.0 parts of copolymer #2, 15.0 parts of isopropyl alcohol, 1.0 part nonoxynol-9, 4.0 parts propylene glycol, and 55.0 parts water. Fifty parts of carbon dioxide are added to the aerosol container through the valve. When this composition is sprayed from the aerosol container onto a cervix, a thin film forms after spraying, completely coating the cervix. This becomes a foamy gel as the solvent evaporates. The composition effectively immobilizes spermatazoa.

EXAMPLE 4

Example 2 is repeated using 100 parts of a liquid composition comprising 17.0 parts of copolymer designated herein as copolymer #3, 1.0 part nonoxynol-9, and 82 parts water. One hundred parts of carbon dioxide are added to the aerosol container through the valve.

The polyoxyethylene-polyoxypropylene copolymer employed, designated herein as copolymer #3, is a polyoxyethylene adduct of a polyoxypropylene hydrophobic base having a molecular weight of said base of about 4000 and wherein the oxyethylene content is about 60 percent of the total weight of the molecule. The polyoxypropylene hydrophobic base is prepared by reacting propylene oxide with a propanediol initiator. When this composition is sprayed from the aerosol container onto a cervix a thin film forms after spraying completely coating the cervix. This becomes a foamy gel as the solvent evaporates. The composition effectively immobilizes spermatazoa.

EXAMPLE 5

Example 2 is repeated using 100 parts propellant and 50 parts of the liquid composition substituting for copolymer #2 a polyoxyethylene-polyoxypropylene copolymer, designated herein as copolymer #4, having a hydrophobe molecular weight of 3500 and wherein the oxyethylene groups constitute about 90 percent of the total copolymer weight. When this composition is sprayed from the aerosol container, a thin film forms after spraying on a cervix which coats completely. This becomes a foamy gel as the solvent evaporates. The composition is effective in immobilizing spermatazoa.

EXAMPLE 6

Example 5 is repeated using 25 parts propellant and 100 parts of the liquid composition.

EXAMPLE 7

Example 2 is repeated with the exception that the liquid composition consists of 25.0 parts of copolymer #2, 10 parts isopropyl alcohol, 10.0 parts of glycerine, 1.0 part of nonoxynol-9, 4.0 parts of acetone and 50 parts of water. Fifty parts of methylene chloride propellant are subsequently added to the aerosol container. When this composition is sprayed from the aerosol container, a thin film forms after spraying on a cervix which completely coats the cervix. This becomes a foamy gel as the solvent evaporates. The composition is effective in immobilizing spermatazoa.

EXAMPLE 8

A liquid composition is prepared comprising 15.0 parts of a polyoxyethylene-polyoxypropylene copolymer, 40 parts of methylethylether, 1.0 part of nonoxynol-9, and 44 parts of water.

Fifty parts of the above liquid are placed in an aerosol container, the container is pressurized and sealed with a valve and 25 parts of a propellant, namely dimethylether, are added through the valve. The contents are shaken and 1 ml sprayed onto the cervix. A thin film forms initially completely coating a cervix after which the dimethylether and ethylmethylether evaporate whereby a foamy gel forms on the surface. The composition effectively immobilizes spermatazoa.

The polyoxyethylene-polyoxypropylene copolymer employed, designated herein as copolymer #5, is a polyoxyethylene adduct of a polyoxypropylene hydrophobic base having a molecular weight of said base of about 3000 and wherein the oxyethylene content is about 60 percent of the total weight of the molecule. The polyoxypropylene hydrophobic base is prepared by reacting propylene oxide with a propanediol initiator.

EXAMPLE 9

A liquid composition is prepared comprising 36 parts of a polyoxyethylene-polyoxypropylene copolymer, 20 parts of methylethylether, 0.1 part of nonoxynol-9, and 43.9 parts of water.

One hundred parts of the above liquid are placed in an aerosol container, the container is pressurized and sealed with a valve and 25 parts of a propellant, namely dimethylether, are added through the valve. The contents are shaken and 1 ml sprayed onto the cervix. A thin film forms initially completely coating a cervix after which the dimethylether and ethylmethylether evaporate whereby a foamy gel forms on the surface. The composition effectively immobilizes spermatazoa.

The polyoxyethylene-polyoxypropylene copolymer employed, designated herein as copolymer #6, is a polyoxyethylene adduct of a polyoxypropylene hydrophobic base having a molecular weight of said base of about 3000 and wherein the oxyethylene content is about 65 percent of the total weight of the molecule. The polyoxypropylene hydrophobic base is prepared by reacting propylene oxide with a propanediol initiator.

EXAMPLE 10

A composition is prepared comprising 15.0 parts of a polyoxyethylene-polyoxypropylene copolymer, 30 parts of glycerine, 0.1 part of nonoxynol-9, and 54.9 parts of water. The composition is cooled to 5° C.

One hundred parts of the above liquid are placed in an aerosol container, the container is pressurized and sealed with a valve and 25 parts of a propellant, namely dimethylether, are added through the valve which dissolves the above composition to form a liquid. The contents are shaken and 1 ml sprayed onto the cervix. A thin film forms initially completely coating a cervix after which the dimethylether and ethylmethylether evaporate whereby a foamy gel forms on the surface. The composition effectively immobilizes spermatazoa.

The polyoxyethylene-polyoxypropylene copolymer employed, designated herein as copolymer #7, is a polyoxyethylene adduct of a polyoxypropylene hydrophobic base having a molecular weight of said base of about 4000 and wherein the oxyethylene content is about 70 percent of the total weight of the molecule. The polyoxypropylene hydrophobic base is prepared by reacting propylene oxide with a propanediol initiator.

The embodiments of the invention in which an exclusive privilege or property is claimed are defined as follows:

1. A pressurized contraceptive composition in an aerosol container capable of forming a spray upon release of pressure therefrom which composition is a liquid inside the container and forms a gel on contact with living tissue and which comprises by weight about 20 to 60 percent water, about 20 to 80 percent propellant, 0 to about 40 percent of a non-propellant volatile solvent, about 0.02 to about 1.5 percent of a sperm function inhibitor, and 7.5 to 30 percent polyoxyethylene-polyoxypropylene copolymer of the formula:

$$Y[(H_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 3000 to 4500 and the value of m is such that the oxyethylene groups constitute about 50 to 90 percent of the total weight of the compound.

2. The composition of claim 1 including about 1.0 to 30 percent of at least one adjuvant.

3. The composition of claim 1 wherein Y is propylene glycol whereby the resulting compounds have the structure $HO(C_2H_4O)_m(C_3H_6O)_n(C_2H_4O)_mH$ wherein n has a value such that the oxypropylene groups have a molecular weight of about 3000 to 4500 and m has a value such that the oxyethylene groups constitute about 50 to 90 percent of the total weight of the compound.

4. The composition of claim 3 including about 1.0 to 30 percent of at least one adjuvant.

5. The composition of claim 3 wherein the amount of non-propellant volatile solvent is about 10 to 25 percent.

6. The composition of claim 5 including about 5.0 to 10 percent of at least one adjuvant.

7. A pressurized contraceptive composition in an aerosol container capable of forming a spray upon release of pressure therefrom which composition is a liquid inside the container and forms a gel on contact with living tissue comprising by weight about 20 to 80 percent propellant about 20 to 60 percent water, about 0.02 to 1.5 percent sperm function inhibitor and about 7.5 to 30 percent polyoxyethylene-polyoxypropylene copolymer of the formula:

$$HO(C_2H_4O)_m(C_3H_6O)_n(C_2H_4O)_mH$$

wherein n has a value such that the molecular weight of the oxypropylene groups is from about 3000 to 4500; and the value of m is such that the oxyethylene groups constitute about 50 to 90 percent of the total weight of the compound and the water:copolymer ratio is not greater than about 5.7:1.

8. The composition of claim 7 including about 10 to 30 percent of at least one adjuvant.

9. The composition of claim 7 including about 5.0 to 10 percent of at least one adjuvant.

10. A contraception process comprising spraying a gel composition in liquid form from an aerosol container onto a cervix, whereby a gel is formed on contact therewith, said composition comprising by weight about 20 to 60 percent water, about 20 to 80 percent propellant, 0 to about 40 percent of a non-propellant volatile solvent, 0 to about 1.5 percent sperm function inhibitor and about 7.5 to 30 percent of a polyoxyethylene-polyoxypropylene copolymer of the formula:

$$Y[(C_3H_6O)_n(C_2H_4O)_mH]_x$$

wherein n has a value such that the molecular weight of the oxypropylene groups is from about 3000 to 4500 and the value of m is such that the oxyethylene groups constitute about 50 to 90 percent of the total weight of the compound.

11. The contraception process of claim 10 wherein Y is propylene glycol whereby the polyoxyethylene-polyoxypropylene copolymer has the structure $$HO(C_2H_4O)_m(C_3H_6O)_n(C_2H_4O)_mH$$

wherein n has a value such that the oxypropylene groups have a molecular weight of about 3000 to 4500 and m has a value such that the oxyethylene groups constitute about 50 to 90 percent of the total weight of the compound.

12. The process of claim 11 including 1.0 to about 30 percent of at least one adjuvant.

13. The process of claim 11 wherein the amount of non-propellant volatile solvent is about 10 to 25 percent.

14. The process of claim 13 including about 5.0 to 10 percent of at least one adjuvant.

15. A contraception process comprising spraying a gel composition in liquid form from an aerosol container onto a cervix whereby a gel is formed on contact therewith, said composition comprising by weight about 20 to 80 percent propellant, about 20 to 60 percent water, 0 to about 1.5 percent sperm function inhibitor and about 7.5 to 30 percent polyoxyethylene-polyoxypropylene copolymer of the formula:

$$HO(C_2H_4O)_m(C_3H_6O)_n(C_2H_4O)_mH$$

wherein n has a value such that the molecular weight of the oxypropylene groups is from about 3000 to 4500; and the value of m is such that the oxyethylene groups constitute about 50 to 90 percent of the total weight of the compound and the water:copolymer ratio is not more than about 5.7:1.

16. The process of claim 15 wherein said composition includes about 1.0 to 30 percent of at least one adjuvant.

UNITED STATES PATENT AND TRADEMARK OFFICE
CERTIFICATE OF CORRECTION

PATENT NO. : 4,585,647
DATED : April 29, 1986
INVENTOR(S) : Irving Rudolf Schmolka It is certified that error appears in the above-identified patent and that said Letters Patent is hereby corrected as shown below:

Claim 1, line 51, column 9, revise formula to read:

$$Y\left[(C_3H_6O)_n(C_2H_4O)_mH\right]_x$$

Signed and Sealed this

Fifth Day of August 1986

[SEAL]

Attest:

DONALD J. QUIGG

Attesting Officer

Commissioner of Patents and Trademarks